United States Patent [19]

Taura

[11] 4,268,272

[45] May 19, 1981

[54] EXOTHERMIC COMPOSITION AND WARMING BAG CONTAINING THE SAME

[75] Inventor: Miyako Taura, Chigasaki, Japan

[73] Assignees: Eiichi Ito; Teruchika Taura, both of Japan

[21] Appl. No.: 41,344

[22] Filed: May 22, 1979

[51] Int. Cl.³ .............................. F24J 1/00; F24J 3/04
[52] U.S. Cl. .................................... 44/3 R; 126/204; 126/206
[58] Field of Search ................. 44/3 R, 3 A, 3 B; 126/204, 206

[56] References Cited

U.S. PATENT DOCUMENTS

| | | | |
|---|---|---|---|
| 1,481,208 | 1/1924 | Johnson | 126/204 X |
| 1,525,168 | 2/1925 | Davison | 126/204 X |
| 1,620,581 | 3/1927 | Smith | 126/204 X |
| 3,301,250 | 1/1967 | Glasser | 44/3 R |
| 3,976,049 | 8/1976 | Yamashita et al. | 44/3 A |

Primary Examiner—Carl F. Dees

[57] ABSTRACT

This invention is an exothermic composition prepared by mixing an iron powder with a mixed fibrous and carbonaceous powder as impregnated with a solution prepared by dissolving a proper amount of a neutral salt in an aqueous solution of an alkali or alkaline weak acid salt so as to mature when left sealed and a warming bag wherein said exothermic composition is contained in a ventilative inner bag provided in a part with a group of ventilating holes and a nonventilative label covering it and this inner bag is contained in a nonventilative outer bag.

3 Claims, 2 Drawing Figures

EXOTHERMIC COMPOSITION AND WARMING BAG CONTAINING THE SAME

BACKGROUND OF THE INVENTION (a) Field of the Invention

This invention relates to improvements of an exothermic composition for warming bags warming a human body by using as a heat source a compound of a metal powder generating heat in the presence of water and oxygen and a warming bag containing the same.

(b) Description of the Prior Art

There is already known a warming bag wherein a composition prepared by adding an aqueous solution of a salt of a metallic halide (such as NaCl, KCl, $CaCl_2$, $FeCl_3$, $FeCl_2$, $MgCl_2$, or $AlCl_3$) or a metallic sulfate (such as $Na_2SO_4$, $K_2SO_4$, $Fe(SO_4)_3$, $FeSO_4$ or $MgSO_4$) to a mixture of active carbon with an exothermic metal (such as an iron powder or the like) is contained in a single bag so as to generate heat by the introduction of air. However, when such exothermic composition is left as insulated all from air, hydrogen will be generated gradually and continuously, will accumulate in the bag, will become high in the concentration with the lapse of days, will inflate the bag occasionally and will have a danger of ingnition and explosion during the preservation. The merchandised conventional warming bag is mostly of such structure that an exothermic metal and a reaction assistant are contained as separately sectioned from each other in a ventilative inner bag which is enclosed with a nonventilative outer bag. When it is to be used, the outer bag will have to be broken and the inner bag taken out will have to be shaken and kneaded to mix the contents much to the trouble. In case the mixing is insufficient, the heat generation lasting time will be reduced and the iron powder will become like a block and will give a different feeling. The charging structure is so complicated that the production rate can not be increased and the cost is high. There are such defects.

SUMMARY OF THE INVENTION

An object of the present invention is to provide an exothermic composition wherein an exothermic metal and an exothermic assistant are not sectioned from each other but are mixed all together, such exothermic characters as a warm feeling and heat generation durability are not impaired and there is no danger of ignition and explosion to eliminate the defects of the conventional warming bag.

As a means of attaining this object, there has been invented an exothermic composition for warming bags characterized by being prepared by mixing 20 to 25 parts by weight of an iron powder with a mixed fibrous and carbonaceous powder as impregnated with a solution prepared by dissolving a proper amount of a neutral salt in 8 to 15 parts by weight of an aqueous solution of a 0.05 to 1 normal alkali or alkaline weak acid salt and leaving the mixture as sealed to mature. The exothermic composition according to the present invention has brought about the below mentioned effects:

(I) It is possible to produce a warming bag wherein, as the exothermic composition is improved by the above described means, even though the exothermic metal and reaction assistant are mixed together in a bag, the generation of hydrogen can be inhibited and, even if it is stored for a long time, there will be no danger of ignition and explosion and the exothermic performances will not be impaired.

(II) The exothermic metal (iron powder) and reaction assistant (the aqueous salt solution, carbonaceous and fibrous materials, water and others) are uniformly mixed, the generation of hydrogen is prevented by adding a proper amount of the alkali or alkaline weak acid salt to mature, therefore the quality of the product does not fluctuate and a highly efficient heat generation durability and an excellent warm feeling are shown.

(III) As the exothermic composition is integrally mixed, such charging structure of the exothermic composition as (a) a means of containing it in an inner bag having a ventilating part in a portion and packing and sealing the inner bag with a nonventilative outer bag or (b) a means of containing it in a nonventilative bag having a ventilating part in a portion on which a nonventilative label is pasted is simple, an ordinary automatically made bag can be charged easily at a high speed and the production cost can be remarkably reduced as compared with the sectioned charged conventional warming bag.

(IV) In the case of (III) (a), the inner bag is taken out of the outer bag and can be used as it is as fitted to the human body. In the case of (III) (b), the label is peeled off the inner bag which can be used as it is as fitted to the human body.

Therefore, the warming bag according to the present invention is much simpler in the using operation than the sectioned charged conventional warming bag article.

BRIEF DESCRIPTION OF THE DRAWINGS

The drawings show an embodiment of the present invention.

DESCRIPTION OF THE PREFERRED EMBODIMENTS

Figure 1:
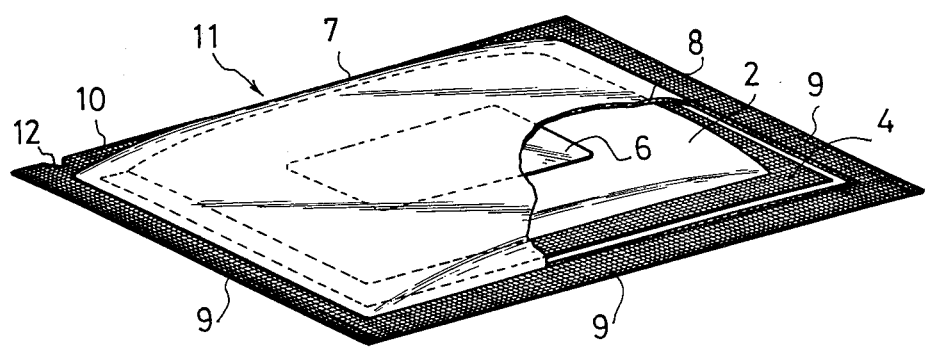
FIG. 1 is a partly sectioned perspective view of a warming bag.

Embodiments of the exothermic composition of the present invention shall be explained in the following. That is to say, the experiment results of comparing respectively the exothermic performances and the amounts of hydrogen generated as insulated from air (as during the storage) of the conventional exothermic composition and the exothermic composition of the present invention are mentioned in the following:

(1) Method of measuring the amount of generated hydrogen.

A container having an inlet pipe and outlet pipe was charged in the central portion with a fixed amount of each sample so that nitrogen gas might contact and pass it, was arranged in a thermostatic tank and was kept at a predetermined temperature, bottle nitrogen was humidified to be of a fixed humidity in a fixed flow volume and was piped to be fed into the inlet pipe, the gas having passed in contact with the sample was piped to pass through a gas-chromatograph and flow meter connected to the outlet pipe and the amount of generated hydrogen per hour delivered by the sample was calculated from the analysis value of the hydrogen concentration in the outlet nitrogen gas and the gas flow measured value.

(2) Method of measuring the heat generating manner (warm feeling test).

A rectangular flat inner bag of outer peripheral effective dimensions of 8 cm. wide×12 cm. long was made by thermally fusing a film made by laminating a nonwoven fabric (of 40 g./m$^2$.) and a polyethylene film (of 70 microns) on the outer periphery except one end, had 230 pinholes of a diameter of 0.5 mm. made through one surface so as to be ventilative, was charged with a fixed amount of each sample, was thermally fused on the end, was then put into an outer bag of a nonventilative film and was sealed.

In the testing method, the inner bag was taken out of the outer bag, was once gripped down to introduce air into the bag and was closely fitted to a human body through an underwear, the time when the inner bag was taken out of the outer bag was made a starting point, the time until a pleasant temperature was reached from it was made a rising time, then the time until the temperature lowered to 40° C. was made a heat generation lasting time and each sample was tested under the same conditions.

(3) Conditions of preparing the sample.

A mixture of 29 g. of an iron powder, 4.5 g. of an active carbon powder as a carbonaceous material and 6 g. of a wood powder as a fibrous material was made common to the respective samples. The above described mixture of the active carbon and wood powder was impregnated with an aqueous solution of a salt shown in the following table or a solution prepared by dissolving hydrochloric acid in a normal solution of an alkali or alkaline weak acid salt and was mixed with the iron powder to prepare a sample. Each sample was left to mature as sealed for 15 hours and was tested. That is to say, the known conventional exothermic composition was made a reference and had (NaOH) and Ba(OH)$_2$ as alkalis and Na$_2$CO$_3$, NaHCO$_3$ and Na$_3$PO$_4$ as alkaline weak acid salts added to it.

Known exothermic composition samples (a, b), samples of the present invention to which an alkali or an alkaline weak acid salt was added (c to j) and samples containing no salt and having had an alkali or an alkaline weak acid salt added (k and l) for information were prepared and were tested under the same conditions.

| Sample sign | Added amount of the salt (in g.) | Added amount of the alkali or alkaline weak acid salt (in ml.) | |
|---|---|---|---|
| a | FeCl$_3$ | 1.5 | Pure water | 10 |
| b | NaCl | 1.5 | " | 10 |
| c | " | " | 1N NaOH | |
| d | " | " | 0.1N NaOH | |
| e | " | " | 0.05N NaOH | |
| f | " | " | 0.1N Ba(OH)$_2$ | |
| g | " | " | 1N Na$_2$CO$_3$ | |
| h | " | " | 0.1N Na$_2$CO$_3$ | |
| i | " | " | 0.1N NaHCO$_3$ | |
| j | " | " | 0.1N Na$_3$PO$_4$ | |
| k | None | 0 | 1N NaOH | |
| l | None | 0 | 1N NaHCO$_3$ | |

(4) Test results.

(I) Amount of generated hydrogen.

As the amount of generated hydrogen of each exothermic composition showed a stabilized valve in about 50 hours after nitrogen gas began to be fed and passed, the measured valve of each sample in 50 hours from the beginning was shown. The temperature of the composition was held at the room temperature (18° C.) and 40° C. The humidity was held at the atmospheric pressure saturation at the testing temperature.

| | Amount of generated hydrogen (in ml./hr.) | |
|---|---|---|
| Sample sign | At the room temperature (18° C.) | At 40° C. |
| a | 1.2 | 3.1 |
| b | 0.15 | 0.3 |
| c | 0 | 0.001> |
| d | 0.014 | 0.025 |
| e | 0.035 | 0.06 |
| f | 0.04 | 0.038 |
| g | 0.005 | 0.024 |
| h | 0.03 | 0.063 |
| i | 0.035 | 0.06 |
| j | 0.02 | 0.04 |
| k | 0 | 0 |
| l | 0 | 0 |

(II) Exothermic performances.

| Sample sign | Rising time (in minutes) | Lasting time (in hours) | Warm feeling |
|---|---|---|---|
| a | 3 | 20 | Pleasant (rather high in the temperature) |
| b | 5 | 20 | Pleasant |
| c | 18 | 36 | Rather low |
| d | 3 | 27 | Pleasant |
| e | 5 | 26 | Pleasant (rather high in the temperature) |
| f | 3 | 24 | Pleasant |
| g | 17 | 32 | Rather low |
| h | 3 | 28 | Pleasant |
| i | 4 | 25 | Pleasant |
| j | 3 | 24 | Pleasant (rather high in the temperature) |
| k | None | 0 | No heat generation |
| l | None | 0 | No heat generation |

When an aqueous solution of an alkali of 0.05 to 1 N was added to mature the composition, the amount of generated hydrogen of the exothermic composition could be held to be smaller than the amount of hydrogen permeated through the nonventilative outer bag film and the danger could be eliminated.

When the nonventilative bag was charged with each of the compositions (c to j) of the present invention and was left at the normal temperature for one year, the bag was not seen to inflate, the hydrogen concentration within the bag was shown to be less than 0.1% and it was confirmed that there was no danger. On the other hand, the hydrogen concentration within the bag charged with each of the known compositions (a and b) was shown to be 5 to 9%.

The aqueous 1 N alkali solution additive was long in the heat generation duration but was late in the rising and was rather low in the warm feeling. But the 0.1 N alkali or alkaline weak acid salt additive was fast in the rising, was favorable in the warm feeling and was shown to be longer in the heat generation duration than the known compositions. The alkali or alkaline weak acid salt concentration of about 0.1 to 0.5 N showed favorable results in the warm feeling and durability.

Even when the exothermic composition was sealed and matured for 10 hours after being mixed, the generation of hydrogen could be substantially prevented. The sealed maturing for more than 15 hours was preferable. As shown in the control samples (k and l), in case an aqueous solution of an alkali or an alkaline weak acid salt was added to the exothermic comosition from which the salt had been removed, no heat was generated and the amount of the generated hydrogen was zero.

As described above, as compared with the conventional composition, the exothermic composition of the present invention is very low in the amount of generated hydrogen, has no danger and shows excellent exothermic performances. In the production, the product of the present invention can be made at a bag charging rate twice as high as the conventional article (charged as sectioned) and can be remarkably reduced in the production cost.

Figure 2:
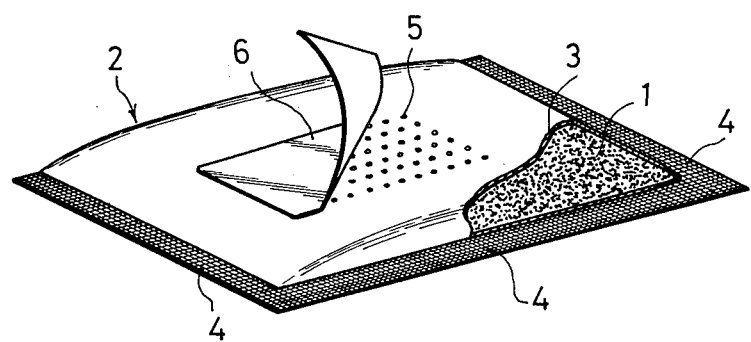
FIG. 2 is a partly sectioned perspective view of an inner bag.

An embodiment of the warming bag containing the above mentioned exothermic composition shall be explained in the following with reference to the drawings in which:

FIG. 1 is a partly sectioned perspective view of a warming bag;

FIG. 2 is a partly sectioned perspective view of an inner bag of the warming bag.

The formation is as mentioned below.

1 is an exothermic composition prepared by mixing 25 g. of an iron powder, 4.5 g. of active carbon, 6 g. of a wood powder and 1.5 g. of table salt, adding 10 c.c. of 0.1 N NaOH to the mixture, putting the mixture in a sealed container and then leaving it to mature. This exothermic coposition 1 is contained in an inner bag 2. The inner bag 2 is made of the above mentioned sample, that is, a nonventilative film 3 formed of a laminated film of a nonwoven fabric of 40 g./m$^2$ and polyethylene of 70 microns is used, is made a flat rectangle of effective outer peripheral dimensions of 8 cm. long × 12 cm. wide and is thermally fused 4 on the three sides except one side, has a ventilating hole group 5 of about 230 pinholes of a diameter of 0.5 mm. formed on the surface on one side and has a nonventilative label 6 pasted with an acrylic resin paste on this ventilating hole group.

7 is an outer bag which contains the above mentioned inner bag 2 and in which a nonventilative film 8 formed of a transparent KOPET film made by laminating polypropylene of 15 microns on the outside and polyethylene of 50 microns on the inside and coated with vinylidene chloride is used, is made a rectangle of effective outer peripheral dimensions of 11 cm. long × 16 cm. wide and is thermally fused 9 on the three sides except one side. The inner bag 2 charged with the above mentioned exothermic composition 1 is contained in this outer bag 7 and then the outer bag 7 is thermally fused on the remaining one side to form a warming bag 11. 12 ia a notch made on the outer bag 7. One side of the outer bag 7 is cut off through this notch 12 and the inner bag 2 is taken out to use the warming bag 11.

EXAMPLES

Six samples of the above mentioned exothermic composition were prepared. Three inner bags having no label and three inner bags pasted with labels were charged with the respective samples under the same conditions, were then thermally sealed and were inserted into the respective outer bags and the outer bags were thermally sealed to make a total of six sealed samples.

Long leaving tests were started on Apr. 1, 1977. In order to confirm the heat generation duration in the use at the time of the beginning, each of the bag without the label and the bag with the label was used. Then each of the bag without the label and the bag with the label was arranged by the side of a sunny window. Each of the bag without the label and the bag with the label was arranged within a shady room. How the appearance and the heat generation durability varied when they were left for about one year was observed and confirmed. The results were as follows:

| | Appearance Tests | | | |
|---|---|---|---|---|
| | Sample without label | | Sample with label | |
| Sample name Arranging place Elapsing time | By the side of window | Within shady room | By the side of window | Within shady room |
| April, 1977 | Nothing wrong | Nothing wrong | Nothing wrong | Nothing wrong |
| June, 1977 | Nothing wrong | Nothing wrong | Nothing wrong | Nothing wrong |
| August, 1977 | Water drops accumulated within the outer bag and the inner bag was wet | Nothing wrong | Nothing wrong | Nothing wrong |
| October, 1977 | The inner bag was wet by ⅔ and a large amount of water was present within the outer bag | The outer bag was cloudy on the inside surface and the inner bag was partly wet | Nothing wrong | Nothing wrong |
| December, 1977 | The inner bag was wet by ⅔ and a large amount of water was present within the outer bag | The outer bag was cloudy on the inside surface and the inner bag was partly wet | Nothing wrong | Nothing wrong |
| February, 1978 | The inner bag was wet by ⅔ and a large amount of water was present within the outer bag | The outer bag was cloudy on the inside surface and the inner bag was partly wet | Nothing wrong | Nothing wrong |
| April, 1978 | The inner bag was wet by ⅔ and a large amount of water was present within the outer bag | The outer bag was cloudy on the inside surface and the inner bag was partly wet | Nothing wrong | Nothing wrong |
| June, 1978 | The inner bag was wet by ⅔ and a large amount of water was present within the outer bag | The outer bag was cloudy on the inside surface and the inner bag was partly wet | Nothing wrong | Nothing wrong |

| Practice Tests (Heat generation duration in the use) | | | |
|---|---|---|---|
| Sample without label | | Sample with label | |
| April, 1977 | 27H | | 27H |
| June, 1978 | By the side of window 12H | With shady room 18H | By the side of window 24H | With shady room 27H |

When the sample without the label was arranged by the side of the sunny window, with the rise of the temperature, the water content in the exothermic composition evaporated severely, when the temperature lowered at night, the inner bag was wet on the surface with water drops and, with the lapse of days, the amount of water on the outside increased to stain the surface of the bag, the commodity valve was remarkably reduced and the heat generation durability in the use remarkably deteriorated. On the other hand with the sample with the label, irrespective of the shady room or the window side, the inner bag was not wet on the surface with water drops, the heat generation durability did not substantially vary as compared with that at the beginning of the test and the sample was confirmed to be enduable to a long preservation.

I claim:

1. An exothermic composition for warming bags characterized by being prepared by mixing 20 to 25 parts by weight of an iron powder with a mixed fibrous and carbonaceous powder as impregnated with a solution prepared by dissolving a proper amount of a neutral salt in 8 to 15 parts by weight of an aqueous solution of a 0.05 to 1-normal alkali or alkaline weak acid salt and leaving the mixture as sealed to mature.

2. A warming bag characterized by containing the exothermic composition according to claim 1 in a nonventilative inner bag provided on a part of the surface with a ventilating hole group of pinholes and containing said inner bag in a nonventilative outer bag.

3. A warming bag characterized by containing the exothermic composition according to claim 1 in a nonventilative inner bag provided on a part of the surface with a ventilating hole group of pinholes and a nonventilative label covering the hole group and containing said inner bag in a nonventilative outer bag.

* * * * *